(12) United States Patent
Bornzin

(10) Patent No.: US 10,004,907 B2
(45) Date of Patent: Jun. 26, 2018

(54) AUTOMATIC CAPTURE VERIFICATION WITHIN LEADLESS IMPLANTABLE MEDICAL DEVICES

(71) Applicant: PACESETTER, INC., Sylmar, CA (US)

(72) Inventor: Gene A. Bornzin, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 980 days.

(21) Appl. No.: 14/186,658

(22) Filed: Feb. 21, 2014

(65) Prior Publication Data

US 2015/0238768 A1    Aug. 27, 2015

(51) Int. Cl.
  *A61N 1/37*   (2006.01)
  *A61N 1/05*   (2006.01)
  *A61N 1/375*  (2006.01)
  *A61N 1/372*  (2006.01)

(52) U.S. Cl.
  CPC ........... *A61N 1/371* (2013.01); *A61N 1/3756* (2013.01); *A61N 1/37205* (2013.01); *A61N 1/0565* (2013.01); *A61N 1/0573* (2013.01)

(58) Field of Classification Search
  CPC .... A61N 1/371; A61N 1/3756; A61N 1/0573; A61N 1/0565
  See application file for complete search history.

(56) References Cited

U.S. PATENT DOCUMENTS

| | | | | |
|---|---|---|---|---|
| 4,762,136 A | * | 8/1988 | Baker, Jr. ............. | A61N 1/0573 607/127 |
| 5,649,975 A | * | 7/1997 | Lindegren ............ | A61N 1/0573 600/373 |
| 5,766,229 A | | 6/1998 | Bornzin | |
| 6,144,881 A | * | 11/2000 | Hemming .............. | A61N 1/371 607/28 |
| 6,731,985 B2 | | 5/2004 | Poore et al. | |
| 7,412,287 B2 | | 8/2008 | Yonce et al. | |
| 7,610,092 B2 | | 10/2009 | Cowan et al. | |
| 7,904,153 B2 | | 3/2011 | Greenhut et al. | |
| 7,996,087 B2 | | 8/2011 | Cowan et al. | |
| 8,315,701 B2 | | 11/2012 | Cowan et al. | |
| 8,626,294 B2 | | 1/2014 | Sheldon et al. | |
| 2002/0095190 A1 | | 7/2002 | Bornzin et al. | |
| 2002/0147477 A1 | * | 10/2002 | Pons .................... | A61N 1/3712 607/27 |

(Continued)

*Primary Examiner* — Catherine Voorhees

(57) ABSTRACT

In one example, a leadless implantable medical device (LIMD) generates a cathodal stimulation pulse with anodal recharge for delivery to patient heart tissues using the tip electrode and the anode electrode. The LIMD then verifies capture of the cathodal stimulation pulse and, if capture is not verified, delivers a cathodal backup stimulation pulse with anodal recharge using the tip electrode and the anode electrode. Automatic capture verification is thereby provided within an LIMD to allow for a reduction in the magnitude of stimulation pulses and to extend the lifetime of the device. In one particular example, the anode is a middle portion of a cylindrical case with a surface area sufficient to prevent anodal stimulation. Other portions of the case are coated with an electrically insulating material to render those portions substantially electrically inert. A voltage halver may be used to further reduce power consumption.

18 Claims, 7 Drawing Sheets

(56) References Cited

U.S. PATENT DOCUMENTS

| | | | |
|---|---|---|---|
| 2003/0083708 A1* | 5/2003 | Bradley | A61N 1/3712 607/27 |
| 2003/0139779 A1* | 7/2003 | Sharma | A61N 1/0587 607/9 |
| 2003/0204222 A1* | 10/2003 | Leinders | A61N 1/37252 607/48 |
| 2005/0127638 A1 | 6/2005 | Yonce et al. | |
| 2006/0136004 A1 | 6/2006 | Cowan et al. | |
| 2007/0078490 A1 | 4/2007 | Cowan et al. | |
| 2009/0204170 A1* | 8/2009 | Hastings | A61N 1/0565 607/33 |
| 2010/0063562 A1 | 3/2010 | Cowan et al. | |
| 2010/0228308 A1 | 9/2010 | Cowan et al. | |
| 2012/0116489 A1* | 5/2012 | Khairkhahan | A61N 1/375 607/127 |
| 2013/0030493 A1* | 1/2013 | Sheldon | A61N 1/3712 607/28 |
| 2013/0103106 A1* | 4/2013 | Schotzko | A61N 1/3686 607/2 |
| 2013/0110127 A1 | 5/2013 | Bornzin et al. | |
| 2013/0110219 A1 | 5/2013 | Bornzin et al. | |
| 2013/0116529 A1 | 5/2013 | Min et al. | |
| 2013/0116738 A1 | 5/2013 | Samade et al. | |
| 2013/0116740 A1 | 5/2013 | Bornzin et al. | |
| 2013/0116741 A1 | 5/2013 | Bornzin et al. | |
| 2013/0123872 A1 | 5/2013 | Bornzin et al. | |
| 2013/0138006 A1 | 5/2013 | Bornzin et al. | |
| 2014/0276154 A1* | 9/2014 | Katra | A61B 5/04012 600/509 |
| 2014/0330331 A1* | 11/2014 | Thompson-Nauman | A61N 1/05 607/32 |

\* cited by examiner

AUTOMATIC CAPTURE VERIFICATION WITHIN LEADLESS IMPLANTABLE MEDICAL DEVICES

FIELD OF THE INVENTION

The invention generally relates to leadless implantable medical devices (LIMD) such as leadless pacing devices for implant within the heart.

BACKGROUND OF THE INVENTION

LIMDs are typically small-sized leadless devices configured for direct implant within an organ, such as within a chamber of the heart. LIMDs are generally characterized by the following features: electrodes are affixed or mounted to a can or housing of the device and the entire device is attached or implanted within tissues or organs to be sensed or simulated. In the case of an LIMD for implant within the heart, such devices are typically implanted within the right ventricle (RV) of the heart for delivering pacing pulses to the RV, though LIMDs have also be provided or proposed for implant within other chambers such as the right atrium (RA.) LIMDs configured for implant within the heart to provide electrical pacing are often referred to as leadless pacemakers (LLPM). For generality, the term LIMD will be used herein since aspects of the present disclosure may be applicable to LIMDs for implant into other organs than the heart and for other purposes besides pacing.

LIMDs for implant within the heart are described, for example, in the following: U.S. Patent Application 2013/0123872 of Bornzin et al., entitled "Leadless Implantable Medical Device with Dual Chamber Sensing Functionality"; U.S. Patent Application 2013/0138006 of Bornzin et al., entitled "Single Chamber Leadless Intra-Cardiac Medical Device having Dual Chamber Sensing with Signal Discrimination"; U.S. Patent Application 2013/0116741 of Bornzin et al., entitled "Dual-Chamber Leadless Intra-Cardiac Medical Device with Intra-Cardiac Extension"; U.S. Patent Application 2013/0116740 of Bornzin et al., entitled "Single-Chamber Leadless Intra-Cardiac Medical Device with Dual-Chamber Functionality And Shaped Stabilization Intra-Cardiac Extension"; U.S. Patent Application 2013/0110219 of Bornzin et al., entitled "Unitary Dual-Chamber Leadless Intra-Cardiac Medical Device and Method of Implanting Same"; U.S. Patent Application 2013/0110127 of Bornzin et al., entitled "Multi-Piece Dual-Chamber Leadless Intra-Cardiac Medical Device and Method of Implanting Same"; U.S. Patent Application 2013/0116738 of Samade et al., entitled "Single Chamber Leadless Intra-Cardiac Medical Device with Dual-Chamber Functionality"; and U.S. Patent Application 2013/0116529 of Min et al., entitled "Leadless Intra-Cardiac Medical Device with Built-In Telemetry System."

LIMDs for implant in the RV are usually placed in the RV apex or low RV septum near the apex. Typical examples of such devices have battery capacities that allow for about eight to ten years of pacing. This is deemed adequate but it would be better if the devices could last even longer because removing the device for replacement has various risks and in some cases might be quite challenging. As such, should the battery of an LIMD in the RV become depleted, it might be necessary to implant a second LIMD or implant a conventional pacemaker with leads into the heart, with the various risks, costs and potential complications associated therewith.

Accordingly, it would be desirable to provide systems and methods for reducing the power consumption of LIMDs so as to extend their usable lifetimes, particularly for use with LIMDs for implant within the heart, and it is to these ends that at least some aspects of the invention are directed.

SUMMARY OF THE INVENTION

In an exemplary embodiment, a method is provided for use with an LIMD for implant within a patient wherein the LIMD has a tip electrode and an anode electrode. In one example, the LIMD generates a cathodal stimulation pulse with anodal recharge for delivery to patient tissues using the tip and anode electrodes. The LIMD then verifies capture of the cathodal stimulation pulse and, if capture is not verified, delivers a cathodal backup stimulation pulse with anodal recharge using the tip and anode electrodes. In this manner, beat-by-beat automatic capture verification is provided within an LIMD so as to allow for a reduction in the magnitude of most stimulation pulses and to extend the lifetime of the device. In some specific examples, the magnitude of pulses is set to only 0.25 volts (V) above a predetermined stimulation threshold, rather than 1.0 V above the threshold as might be employed without capture verification. More commonly, 1.7 to 2 times threshold is used for setting the stimulus when performing intermittent manual threshold taking at pacemaker follow-up.

In an illustrative example, the LIMD is sized and equipped for RV implant. Capture verification is achieved, in part, by sensing an electrocardiac signal (such as an intracardiac electrogram (IEGM)) during a predetermined interval or window of time following the cathodal stimulation pulse using the tip electrode of the LIMD with reference to the anode electrode. The sensed electrocardiac signal is then evaluated to determine whether the signal is indicative of an evoked response (ER.) For example, a first derivative of the signal can be assessed and compared against a threshold indicative of an ER (i.e. indicative of capture of the cathodal pulse) using, for example, a biquad amplifier/filter having a center frequency of about 50 hertz (Hz) and a Q-value of about 1.4 or using a digital signal processor. If no ER is detected, a loss of capture (LOC) is thereby indicated. The window of time during which the LIMD analyzes the sensed signal to verify capture extends, in one example, from the end of a recharge period (typically 8 to 12 milliseconds (ms) in duration) following delivery of the cathodal stimulation pulse until a predetermined period of time has elapsed following the pulse, such as 90 ms.

In the illustrative example, the LIMD includes a substantially cylindrical conducting case having the anode electrode provided therein, with the tip electrode extending from a distal end of the case for screw-in insertion into the RV apex heart wall. The anode electrode may comprise, for example, a portion of the case that is not electrically insulated from patient tissues. Conversely, other portions of the case are insulated using a suitable material such as perylene applied by an amount sufficient to render those portions substantially electrically inert. As such, the electrically insulated portions of the case do not form part of, nor function as, an anode. The non-electrically insulated portions of the case form the anode electrode of the device. A pulse generator is coupled to the tip electrode and to the anode electrode of the case for generating a cathodal stimulation pulse for delivery to the RV with anodal recharge. A sensing system is equipped to sense electrocardiac signals using the tip electrode with reference to the anode electrode. An automatic capture verification system is operative to verify capture of the cathodal stimulation pulse based on sensed electrocardiac signals and may include the aforementioned biquad amplifier or digital signal processing components. A backup stimulation pulse system is operative upon loss of capture (i.e. upon failure to detect an expected ER within the ER detection window) to control the pulse generator to generate a cathodal backup stimulation pulse of larger magnitude than the initial stimulation pulse. The backup pulse is also delivered using the tip and anode electrodes with anodal recharge.

Still further, in the illustrative example, a single feedthrough is provided within the case for connecting the tip electrode to the pulse generator and to the sensing system (via suitable interconnection components such as switches or the like.) The anode portion of the case is a cylindrical portion of the case encircling the middle of the device and is provided with surface area sufficient to substantially prevent anodal stimulation, such as a surface area of at least 133 mm². The length of the anode portion along the axis of the device from a proximal to a distal end of the anode portion may be in the range of, e.g., 7 to 8 mm. The tip electrode and the distal end of the anode electrode are spaced apart from one another by an amount in the range of 5 to 17 mm, such as 10 mm. At least a portion of the exterior of the case, excluding the un-insulated anodal portion, is coated in perylene or similar biocompatible insulating compounds by an amount sufficient to electrically insulate the coated portions from patient tissues. The anodal portion of the case is coated (either totally or partially) with a low-polarization coating, such as tin, iridium oxide (IrOx) or platinum black, by an amount sufficient to reduce polarization due to pacing to acceptable levels for capture verification.

Additionally, in the illustrative embodiment, a voltage halver is equipped to selectively half a voltage of power generated by a power supply of the device prior to generation of a cathodal stimulation pulse. The voltage halver may be invoked for pulses of 1.25 V or less. In one example, cathodal pacing pulses are generated at 1.25 V and hence the voltage halver is used, thereby reducing power consumption as compared to devices that do not exploit a voltage halver. If a backup pulse is required, the voltage halver is switched out and a larger voltage pulse of, e.g., 2.0 V is generated. A properly equipped LIMD provided with automatic capture verification a voltage halver can have a power source lifetime of, e.g., of sixteen years or more.

Various examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of LIMD with Automatic Capture Verification

Figure 1:
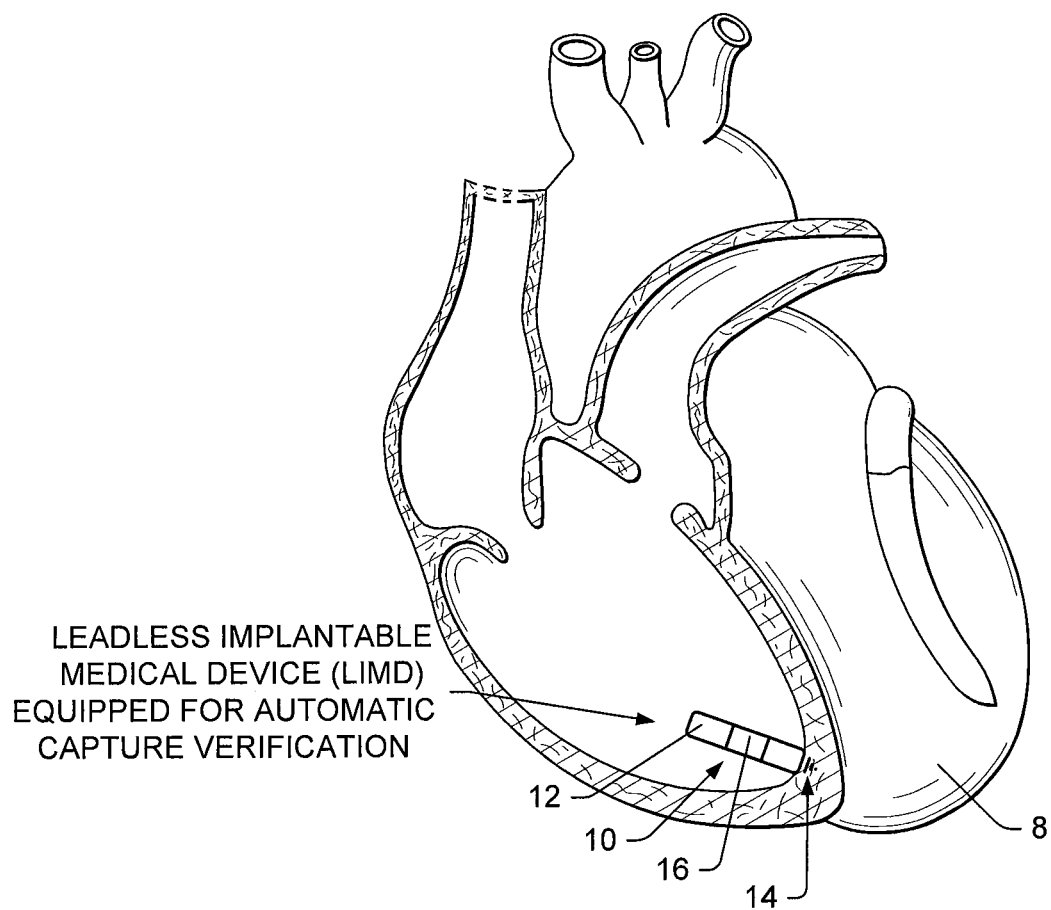
FIG. 1 illustrates an exemplary LIMD implanted within the RV of a heart and equipped for automatic capture verification.
Figure 2:
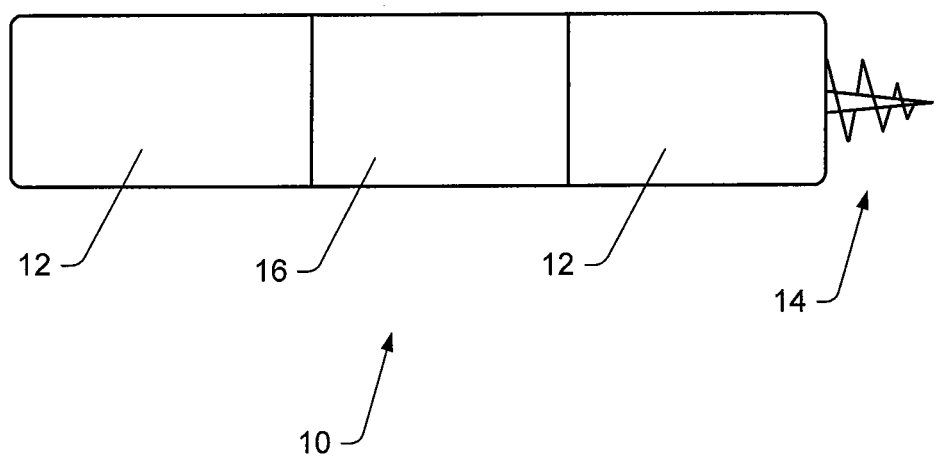
FIG. 2 further illustrates the LIMD of FIG. 1.

FIG. 1 illustrates a heart 8 with an exemplary LIMD 10 equipped for automatic capture verification. FIG. 2 illustrates the LIMD separate from the heart. In the example of FIGS. 1 and 2, LIMD 10 includes a substantially cylindrical case 12 having a tip electrode 14 for affixing the LIMD to the RV myocardium wall, such as in the apex of the RV as shown in FIG. 1. The tip electrode is an active fixation screw-in electrode extending from a distal end of the case and configured to permanent or semi-permanent fixation into heart wall tissues. The LIMD also includes a substantially cylindrical anode electrode 16 encircling the case. As will be explained below, the anode electrode may comprise a portion of an otherwise integral conducting metal case wherein the anode portion includes different coatings from other portions of the case to allow the anode portion to function as an electrode whereas the other portions are substantially electrically insulated from patient tissues. In other implementations, the anode can be a physically separate component mounted to the case and fully electrically isolated from other parts of the case, although such would typically require an additional feedthrough. Internal components of the LIMD, shown and described more fully below, are equipped to sense electrocardiac signals (such as IEGM signals) using the tip and anode electrodes and to deliver electrical stimulation pulses (e.g. pacing pulses) to myocardial tissues using the electrodes. In particular, in the illustrative examples described herein, the internal components of LIMD 10 operate to generate a cathodal stimulation pulse with anodal recharge for delivery to patient tissues using tip electrode 14 and anode electrode 16. The internal components of the LIMD then verify capture of the cathodal stimulation pulse and, if capture is not verified (i.e. an LOC is detected or otherwise indicated), the internal components of the LIMD deliver a cathodal backup stimulation pulse with anodal recharge, also using tip electrode 14 and anode electrode 16. In this manner, automatic capture verification is provided within an LIMD to allow for a reduction in the magnitude of stimulation pulses and to extend the lifetime of the device, as described in further detail below. The automatic capture verification procedure may also be referred to as AutoCapture™.

Although described with respect to an LIMD for implant in the heart, at least some of the systems and techniques described herein are generally applicable to other LIMDs, such as LIMDs for electrically stimulating nerves or other organs where signals responsive to the electrical stimulation can be observed to verify "capture" of the electrical stimulation. Note also that FIGS. 1 and 2 include stylized illustrations that do not necessarily set forth the precise location of the LIMD nor its size or shape relative to anatomical structures.

Capture Verification Considerations for IMDs and LIMDs

At least some IMD engineers studying automatic output regulation using the ventricular ER initially preferred using bipolar sensing of the ER. Bipolar sensing was preferred because the engineers were concerned that unipolar sensing would be confounded by myopotentials masquerading as ERs and this would lead to false positive ER sensing and inappropriate threshold measurement and beat-by-beat capture monitoring. What was observed with bipolar pace and bipolar sensing between the tip and the ring was that, at outputs of at least a few volts, the ERs effectively "disappeared" because anodal stimulation at the ring was triggered. The anodal stimulation at the ring, along with the cathodal stimulation at the tip, resulted in simultaneous depolarization of tissues at both the tip and ring. The simultaneous depolarization at both the tip and ring then substantially cancelled out voltage differences between the anode and cathode, resulted in little or no signal coming out of a differential amplifier used to isolate differences between anodal and cathodal voltage signals.

Figure 3:
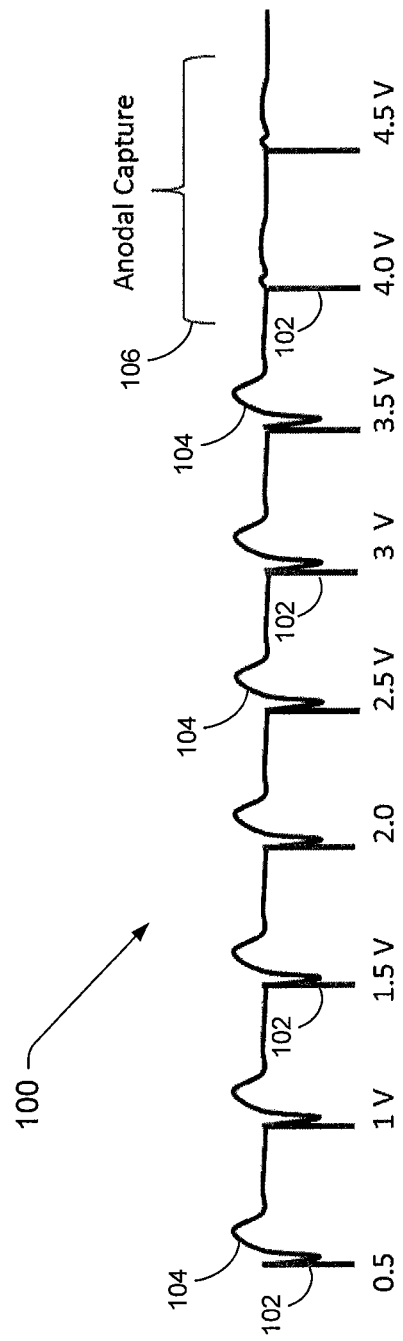
FIG. 3 illustrates various exemplary ERs and other signals that may be detected by the LIMD of FIG. 1 and particularly illustrates a loss of capture due to anodal stimulation that can occur in some LIMDs.

FIG. 3 illustrates a trace 100 generated in accordance with the conventional processing of electrocardiac signals by an IMD, particularly illustrating a false positive "loss of capture" due to anodal stimulation at higher pulse voltages. More specifically, trace 100 includes bipolar pacing with pulses 102 (with exemplary pulse magnitude voltages shown for each pulse) and bipolar sensing of ERs 104. At higher pulse outputs, the anode captures along with the cathode, causing a significant drop in the ER as shown by anodal capture region 106 of trace 100. The significant drop in the ER occurs because the depolarization takes place at both the tip and the ring, effectively cancelling the depolarization within the detection circuitry of the device. In this regard, implantable devices typically employ a differential amplifier to compare the signal on the anode to the signal on the cathode to identify any differences therebetween. Assuming that an ER appears on the cathode but not the anode, the output of the differential amplifier will be a signal showing the ER, which is then detected by appropriate detection circuitry. However, if an ER occurs on both the cathode and anode due to anodal stimulation, then the output of the differential amplifier will be substantially flat.

To avoid this problem of false positive "loss of capture" due to anodal stimulation, at least some engineers of leaded IMDs (such as conventional pacemakers) decided to pace unipolar between the tip of the lead and the device case while maintaining bipolar sensing between the tip and the ring electrodes of the lead. Unipolar pacing between the tip and the device case generally solved the problem of false positive "loss of capture" due to anodal ring stimulation while bipolar sensing avoided myopotential oversensing. (Low polarization electrodes may also be needed to further limit the stimulus artifact due to polarization that persists after stimulation and can obscure the evoked response.) However, the unipolar pacing/bipolar sensing configuration created a new problem: patients would sometimes experience pocket stimulation caused by unipolar pacing between the tip and the device case, at least for IMDs where the device case was implanted within a pocket below the skin with leads implanted within the heart. Another approach that has been suggested is to pace tip to ring and sense ring to case, which can solve the pocket simulation and anodal stimulation problems. However, other issues remain. ER sensing between the ring and the case can result in myopotential oversensing. Furthermore, ring-to-case ER sensing can exhibit ER latency. That is, ERs can be detected too late (i.e. there is too much of a time delay between the pacing pulse and the sensing of the ER due to conduction delays.) Because of the time delay, backup pulses may be delivered later than 90 milliseconds after the pacing pulse, which can be pro-arrhythmic. As such, there are various design comprises when attempting to provide automatic capture verification, at least within pacing systems with leads. These compromises can be avoided or at least substantially reduced by using a properly configured LIMD, as shown in FIGS. 1 and 2 and as described in further detail below.

Table I summarizes exemplary problems and potential resolutions pertaining to implementing automatic capture verification in conventional pacemaker systems employing leads, as well for a leadless system (shown in the last row of the table.) Exemplary technical issues include: 1) ER drop at higher stimulation amplitudes due to anodal stimulation; 2) oversensing of myopotentials; 3) latency between pacing stimulation and the sensing of an ER; 4) pocket stimulation at higher outputs; and 5) the need for low polarization electrodes to avoid anodal stimulation.

TABLE I

| CONFIGURATION FOR PACING AND SENSING | EXEMPLARY PROBLEM(S) | EXEMPLARY PROBLEMS RESOLVED |
|---|---|---|
| Pace: tip to ring<br>Sense ER: tip to ring | ER drop at higher stimulation amplitudes due to anodal stimulation<br>Need for low polarization electrodes for both the anode and cathode electrodes | No oversensing of myopotentials<br>No pocket stimulation at higher outputs<br>No latency between stimulating and sensing of ER |
| Pace: tip to case<br>Sense ER: tip to ring | Pocket stimulation at higher outputs<br>Need for low polarization electrodes for at least the cathode electrode and perhaps the anode electrode | No oversensing of myopotentials<br>No ER drop at higher stimulation amplitude due to anodal stimulation<br>No latency between stimulating and sensing of ER |
| Pace: tip to ring<br>Sense ER: ring to case | Oversensing of myopotentials<br>Long latency stimulating and and sensing of ER | No pocket stimulation<br>No ER drop at higher stimulation amplitude due to anodal stimulation<br>Can use high polarization electrodes |
| Pace: tip to case<br>Sense ER: ring to case | Oversensing of myopotentials<br>Pocket stimulation at higher outputs | No ER drop at higher stimulation due to anodal stimulation<br>Little latency between stimulation and sensing<br>Can use high polarization electrodes |
| Leadless device properly designed configuration for implant within the heart<br>Pace: tip to anode portion of case<br>Sense: tip to anode portion of case | May require low polarization electrodes for the cathode electrode and the possibly the anode | No significant oversensing of myopotentials<br>No pocket stimulation at higher outputs since there is no pocket<br>No significant |

TABLE I-continued

| CONFIGURATION FOR PACING AND SENSING | EXEMPLARY PROBLEM(S) | EXEMPLARY PROBLEMS RESOLVED |
|---|---|---|
| | | latency between stimulating and sensing of ER No significant ER drop at higher amplitude due to anodal stimulation |

Note that capture verification in the context of leaded IMDs is described in, e.g., U.S. Pat. Nos. 6,731,985 and 5,766,229 and in U.S. Patent Publication Nos. 2003/0083708 and 2002/0095190.

Illustrative LIMD Equipped for Automatic Capture Verification

Figure 4:
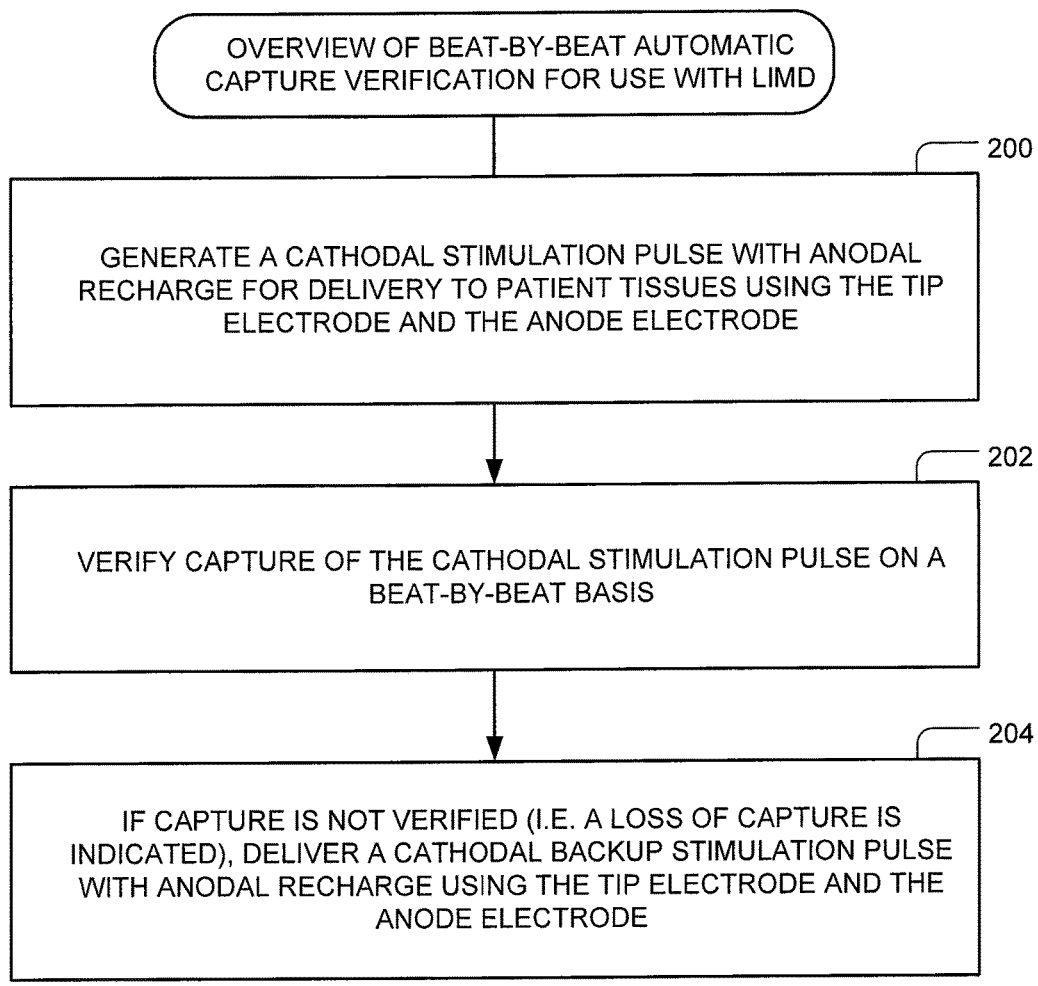
FIG. 4 provides an overview of an automatic capture verification procedure for use with the LIMD of FIGS. 1-2.

Turning now to FIG. 4, an overview of an automatic capture verification procedure for use with the LIMD of FIGS. 1-2 is provided wherein the LIMD addresses the design considerations and concerns discussed above. Beginning at step 200, the LIMD generates a cathodal stimulation pulse with anodal recharge for delivery to patient tissues using the tip electrode and the anode electrode of the LIMD. At step 202, the LIMD verifies capture of the cathodal stimulation pulse and, if capture is not verified (i.e. a LOC is detected), the LIMD delivers a cathodal backup stimulation pulse with anodal recharge using the tip electrode and the anode electrode. By providing automatic capture verification in this manner, the magnitude of pacing pulses can be reduced as compared to those of a similar device without capture verification so as to save power while still substantially ensuring that therapy is properly delivered via any needed backup pulses.

Figure 5:
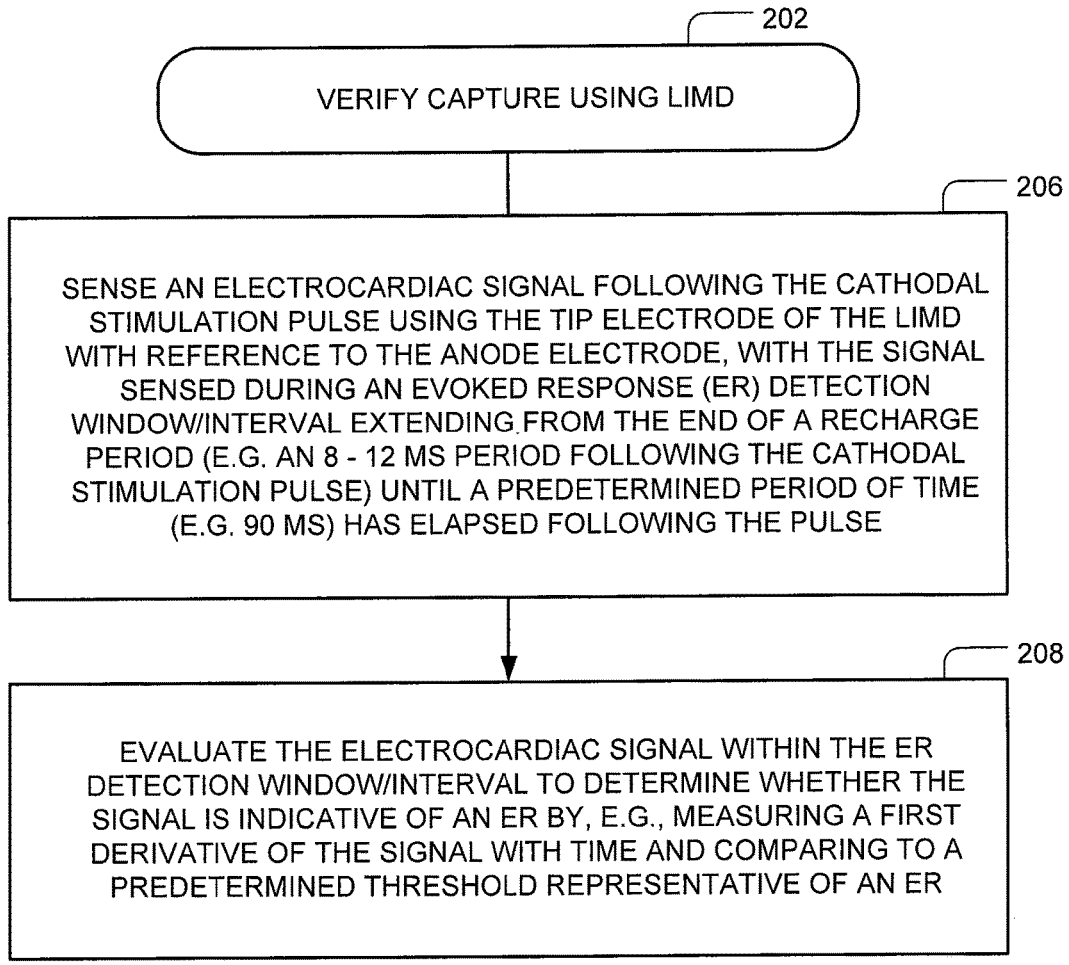
FIG. 5 further illustrates the automatic capture verification procedure of FIG. 4.

FIG. 5 further illustrates exemplary capture verification procedure 202 of FIG. 4. At step 206, the LIMD senses an electrocardiac signal (e.g. IEGM) following the cathodal stimulation pulse using the tip electrode of the LIMD with reference to the anode electrode of the LIMD, with the signal sensed during an ER detection window extending from the end of a recharge period until a predetermined period of time has elapsed following the pulse. The recharge period ends, e.g., 8-12 ms following delivery of the cathodal stimulation pulse. The exact duration of the recharge period (e.g. 10 ms) may be predetermined and preset into the device or, if so equipped, the device may be capable of detecting the end of the recharge period and activating the ER detection window accordingly. In any case, the ER detection window may extend, e.g., until 90 ms after the cathodal stimulation pulse. Hence, for an example where the recharge period is set to 10 ms, the ER detection window is 80 ms long. As noted above, the delivery of a backup pulse beyond 90 ms following the initial stimulation pulse can be pro-arrhythmic and hence is to be avoided. At step 208, the LIMD evaluates the sensed electrocardiac signal within the ER detection window to determine whether the signal is indicative of an ER by, e.g., measuring a first derivative of the signal with time and comparing the measured derivative to a predetermined threshold representative of the upward slope of an ER. If no ER is detected within the window, a backup pulse is delivered (step 204 of FIG. 4.) Accordingly, in this example, a backup pulse is delivered no later than 90 ms after the initial cathodal pulse.

Another cause of false positive "loss of capture" is fusion. During fusion, the intrinsic depolarization of the heart is conducted to the tissue at about the same time as the expected evoked response. Since the conducted depolarization may occur simultaneously at the anode and cathode, the depolarizations effectively cancel one another. This leads to a very small differential signal that the system can interpret erroneously as a loss of capture, thus triggering a backup pulse. In order to reduce the probability of the same thing happening on the next cardiac cycle, the pacemaker may invoke rate hysteresis in which the VVI pacemaker's programmed escape interval is increased automatically upon detecting a loss of capture (whether it is a real loss of capture or a false positive loss of capture.) A pacemaker in VVI mode paces and senses the ventricle and is inhibited by a sensed ventricular event. The rate hysteresis increases the escape interval by about 100 ms. The increased escape interval increases the probability that an intrinsic R-wave will be detected before the end of the escape interval. This prevents fusion and actually saves energy by avoiding pacing pulses and backup pulses. If at any time when the device is operating with an extended escape interval, the extended escape interval times out without detecting an intrinsic depolarization, then a pacing pulse is delivered and the rate hysteresis shortens the extended escape interval to the programmed escape interval. The programmed escape interval may be about 1000 ms when the base rate is 60 pulses per minute. When rate hysteresis extends the escape interval to about 1100 ms, the minimum rate is about 55 beats per minute or more. This scheme is currently used in some VVI pacemakers having beat-by-beat AutoCapture™.

Figure 6:
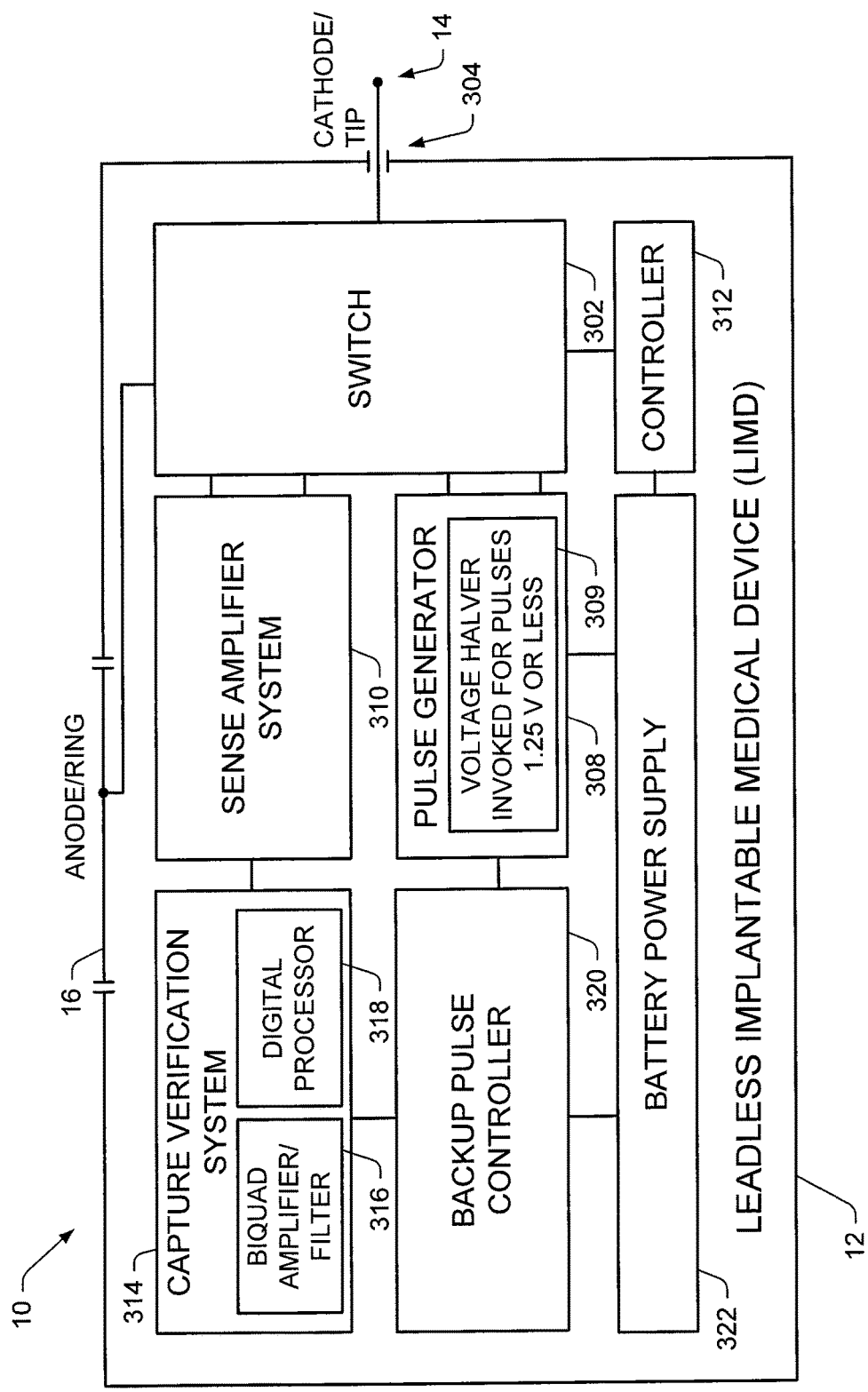
FIG. 6 is a block diagram, partially in schematic form, of components the LIMD of FIG. 1.

FIG. 6 illustrates exemplary components of an LIMD 10 equipped to perform the capture verification methods of FIGS. 4 and 5. The LIMD includes a metal case 12, which includes an anode/ring portion 16 connected to internal components of the device via a switch 302. As already noted, the anode portion can be a portion of the metallic case provided with different coatings to permit it to function as an anode or it may be a physically separate component that is electrically isolated from the rest of the case. LIMD also includes a cathode/tip electrode 14 connected to internal components of the LIMD via switch 302 and via a single feed-through 304. Switch 302 is provided, for example, to allow the LIMD to switch from pacing to sensing by selectively connecting either a pulse generator 308 or a sense amplifier system 310 to the pair of electrodes. The pulse generator may include a voltage halver circuit 309, discussed below, which is only invoked for pulses 1.25 V or less for use in conserving power. The sense amplifier system may include differential amplifiers (not separately shown) for isolating differences between signals on the cathode and on the anode. Switch 302 and all other components of the LIMD may operate under the control of a controller 312, which may be a suitable microcontroller. Depending upon the implementation, the controller may be implemented in hardware or software and may include an application specific integrated circuit (ASIC) or the like.

Insofar as capture verification is concerned, LIMD 10 includes a capture verification system 314 operative to verify capture of pacing pulses generated by the pulse generator based on responsive signals sensed via the sense amplifier system during the aforementioned ER detection window so as to thereby detect a LOC if an ER is not properly found. To this end, capture verification system 314 may include a biquad amplifier/filter 316 and/or a suitable digital processor 318. Typically, only one or the other is provided. Both are shown for the sake of generality. A biquad (or biquadratic) amplifier/filter is a type of linear filter equipped to implement a transfer function corresponding to the ratio of two quadratic functions (and is also sometimes called a "ring of 3" circuit.) Biquad filters are typically active devices and can be implemented with a single-amplifier biquad or two-integrator-loop topology. An example of a biquad filter is the so-called Tow-Thomas filter. The biquad filter can be configured or tuned as needed to detect ERs. In one example, the biquad filter is set to have a Q-value of about 1.4 (or in the range of, e.g., 1.3-1.5) and a center frequency of about 50 Hz (or in the range of, e.g., 40-60 Hz.) A properly tuned and configured biquad filter will detect the positive derivative of the signal output from the sense amplifier system, which is then compared against a predetermined threshold representative of an ER. If the positive derivative exceeds the threshold within the ER detection window, an ER is thereby detected. If the ER detection window elapses without the positive derivative exceeding the threshold, an LOC is thereby detected. A backup pulse controller 320 is then activated to trigger the pulse generator to generate a backup pulse with a substantially larger magnitude than the initial pulse. Note that, if a digital processor 318 is employed, rather than a biquad filter, the digital processor may be a portion of the controller 312. Power is supplied by a battery or other suitable power supply 322. Note that not all components of an actual LIMD are necessarily illustrated in the figure. For example, a capacitor (not shown) may be coupled to the output.

Figure 7:
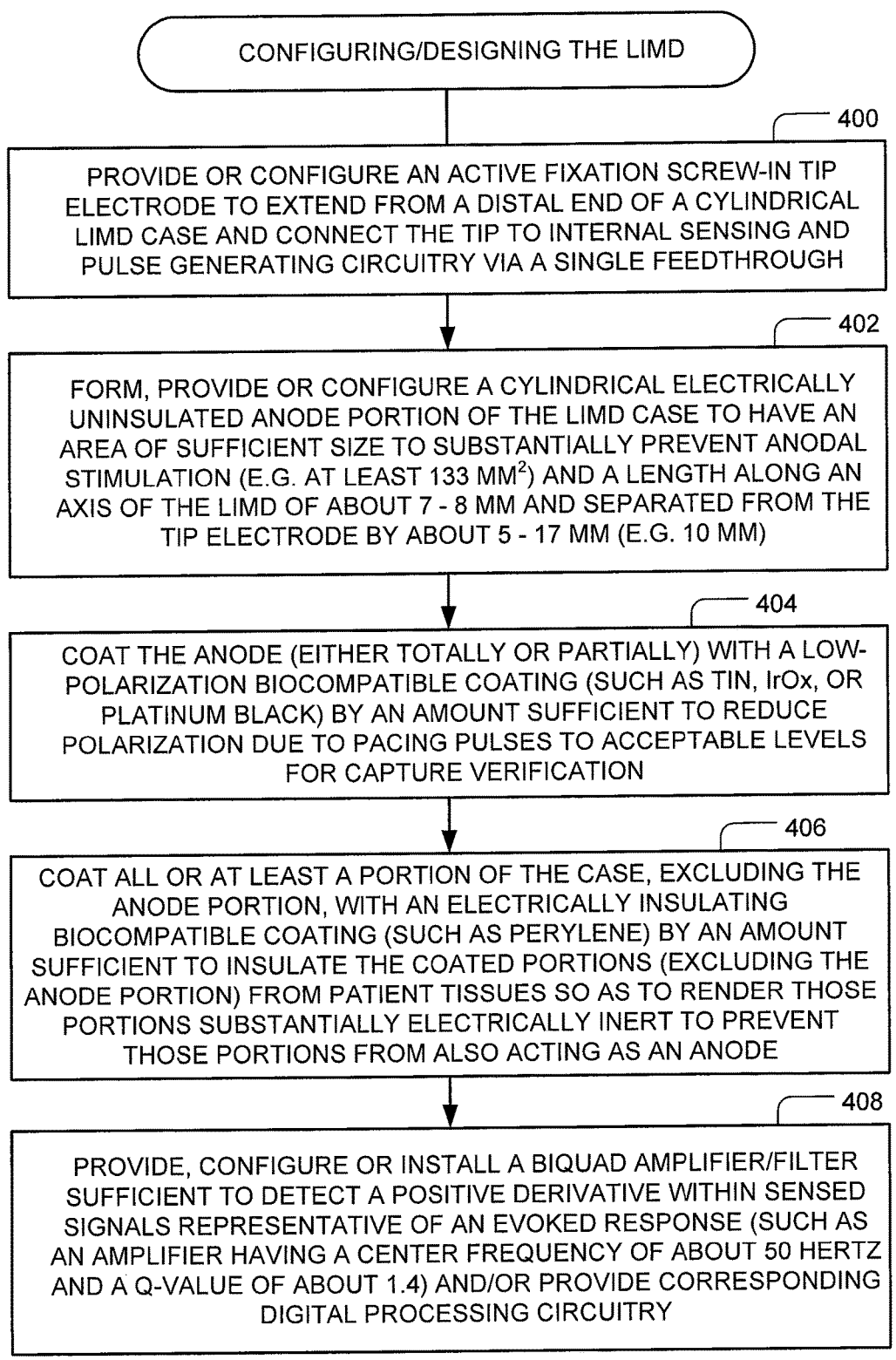
FIG. 7 illustrates selected design and configuration steps pertaining to the LIMD of FIGS. 1-2, particularly identifying various design parameters.

Turning now to FIG. 7, various aspects of the design and configuration of the LIMD will now be summarized and, in some cases, further described. At step 400, an active fixation screw-in tip electrode is provided or configured to extend from a distal end of a cylindrical LIMD case. The tip electrode is connected to internal sensing and pulse generating circuitry via a single feedthrough (and via suitable switches as already indicated.) At step 402, a cylindrical and electrically uninsulated anode portion of the LIMD case is provided or configured to have an area of sufficient size to prevent any significant anodal stimulation (with a size of, e.g., at least 133 mm$^2$) and with a length along an axis of the LIMD of about 7-8 mm and separated from the tip by about 5-17 mm (e.g. 10 mm.) At step 404, the anode is coated (either totally or partially) with a low-polarization biocompatible coating (such as tin, iridium oxide (IrOx), or platinum black) by an amount sufficient to reduce polarization due to pacing pulses to acceptable levels for the purposes of capture verification. At step 406, at least a portion of the case, excluding the anode portion, is coated with an electrically insulating and biocompatible coating (such as perylene) by an amount sufficient to insulate the coated portions (excluding the anode portion) from patient tissues so as to render those portions substantially electrically inert to prevent those portions from also acting as an anode. Perylene or perilene is a type of polycyclic aromatic hydrocarbon having the chemical formula $C_{20}H_{12}$. At step 408, a biquad amplifier/filter is provided, configured or installed in the LIMD that is sufficient to detect a positive derivative within sensed signals representative of an ER, such as a biquad amplifier having a center frequency of about 50 hertz and a Q-value of about 1.4, as noted above. Alternatively, corresponding digital processing circuitry are provided. Insofar as the coatings are concerned, the appropriate amount of coating can be determined without undue experimentation by, for example, applying different amounts of the coating and assessing the effects. Other design parameters, such as the relative spacing of the anode and cathode, can be likewise determined or optimized without undue experimentation.

Still further, note that, if the entire case were uninsulated, P-waves from the atrium might be picked up by the LIMD, particularly if the patient has frequent P-waves during flutter or fibrillation. Hence, preferably only the anode portion is electrically uninsulated. Also, if the space between the uninsulated anode portion of the case and the cathode tip is too long, the ER may be too late and it would be difficult to detect the ER early enough and hence the ER might occur outside of the ER detection window. However, if the space between the cathode tip and the anode is about 10 mm (or in the range of 5-17 mm), the ER detection will likely occur between the end of the recharge (about 8 to 12 ms after the pacing pulse) and 90 ms after the pacing pulse. Conversely, if the insulated region between the anode and the cathode is too short or nonexistent, e.g. less than about 5 mm, the ER may occur during the recharge and will be difficult to detect. The anode may polarize during the pacing pulse so it is preferable to coat or partially coat the anode with a non-polarizable coating. This will help ensure ER detection even with very small ERs. Leaving the entire case uninsulated would result in tissue contact with the case and the tip at the same time and may result in an ER that changes its morphology or has unpredictable morphology.

Based on these and other considerations, current drain can be significantly reduced by operating the LIMD on a narrow stimulation margin in the range of 0.25 volts thereby increasing device longevity. This is achievable using the beat-by-beat automatic capture techniques described above. Consider for example an LIMD with a 220 milliampere hour (mA-hr) battery that has an overhead current of about 1.0 microampere (uA) and is equipped with a voltage halver. The voltage halver divides the battery voltage in two by using two capacitors in series and is used to reduce current delivered from the battery by 50% when the stimulus voltage is at or below 1.25 volts. Assuming the patient in which the LIMD is implanted has a threshold of 1 volt at 0.4 milliseconds, then without capture verification, the device would likely be programmed to 2.0 volts at 0.4 milliseconds (i.e. a 2× safety factor). The device would then use about 1.5 uA for pacing (0.4 ms, 2.0 V, 500 ohms at 60 bpm). Such a device would last about 9.6 years. However, if capture verification is employed as described herein, the device could be programmed to 1.25 volts at 0.4 milliseconds. Since the voltage is at or below 1.25 V, the voltage halver is invoked, thus saving power. The small 0.25 volt safety margin is permitted because the beat-by-beat capture verification automatically delivers a backup pulse if the threshold within the patient should rise above 1.25 V. In this scenario, the expected longevity would thereby grow to 16.6 years, a significant increase relative to the same device without capture verification. (Note that the backup pulse would be at 2.0 V, for example, and hence the backup pulse would not use the voltage halver.)

Capture verification can thereby significantly improve the longevity of the LIMD. For an octogenarian with atrial fibrillation who does not require 100% pacing, the device would likely last well beyond seventeen years and would almost certainly serve the remainder of the patient's life.

Table II summarizes various exemplary parameters for LIMDs with capture verification and ones without. The last five conditions in the table differ between capture verification and non-capture verification systems.

TABLE II

| CONDITIONS | EXEMPLARY VALUES WITHOUT CAPTURE VERIFICATION | EXEMPLARY VALUES WITH CAPTURE VERIFICATION |
|---|---|---|
| Overhead current | 1 uA | 1 uA |
| Battery capacity | 220 mA-hr | 220 mA-hr |
| Battery capacity in uA-years | 25 uA-years | 25 uA-years |
| Battery Voltage | 2.5 volts | 2.5 volts |
| Pacing load | 500 ohms | 500 ohms |
| Percent pacing | 100% | 100% |
| Pulse width | 0.4 ms | 0.4 ms |
| Pacing threshold | 1 volt @ 0.4 ms | 1 volt @ 0.4 ms |
| Voltage halver | not used (available) | yes |
| Safety margin | 2 × threshold | Threshold + 0.25 V |
| Programmed Stimulus | 2 × 1 volt = 2 volts | 1 + 0.25 V = 1.25 volts |
| Pacing current | (2.0 V/.500 Kohms)* .4 ms = 1.6 uA | ½ *(1.25 V/.500 Kohms)* .4 ms = 0.5 uA |
| Longevity | 25 uA-yr/(1 uA 9.6 years | 25 uA-yr/(1 uA years |

In summary, a properly designed leadless pacemaker can provide for automatic capture verification without the complications and compromises required to achieve capture verification in leaded pacemakers and ICDs:

1. ER drop at higher stimulation amplitude due to anodal stimulation can be avoided by using an uninsulated section of the case for the anode that is about 7 to 8 mm long and about 10 mm back from the tip electrode.
2. Oversensing of myopotentials is avoided because the case of the LIMD is totally enclosed in the heart away from skeletal muscle.
3. Latency between stimulating and sensing of ER is avoided by not having a second electrode pair independently detecting the ER and by properly choosing the space between the pacing tip and the anode.
4. Pocket stimulation at higher outputs is avoided because there is no pocket since the device is leadless and implanted in the heart itself.
5. The use of only two electrodes (the tip and the anodal section of the case) eliminates the need for a second feedthrough.

Note that the LIMD will typically require a low polarization tip electrode because it is used for both pacing and sensing the ER; however, adding a low polarization coating to the uninsulated (non-anodal) portion of the case is not required.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A leadless implantable medical device (LIMD) for implant within the heart of a patient, comprising:
    a case, wherein at least a portion of the case being configured as an anode electrode, wherein the anode electrode has a surface area of at least 133 mm² to substantially prevent anodal stimulation;
    a tip electrode extending from the case;
    a pulse generator coupled to the tip electrode and the anode electrode and equipped to generate a cathodal stimulation pulse for delivery to patient tissues with an anodal recharge;
    a sensing system equipped to sense electrocardiac signals using the tip electrode with reference to the anode electrode; and
    an automatic capture verification system operative to verify capture of the cathodal stimulation pulse based on sensed electrocardiac signals.

2. The LIMD of claim 1 further comprising a backup stimulation pulse system operative upon loss of capture to control the pulse generator to generate a cathodal backup stimulation pulse, the backup stimulation pulse also delivered using the tip and anode electrodes with anodal recharge.

3. The LIMD of claim 1 wherein the automatic capture verification system includes a digital processor coupled to the sensing system and equipped to detect a derivative of the evoked response to verify capture.

4. The LIMD of claim 1 wherein the tip electrode comprises an active fixation screw-in electrode.

5. The LIMD of claim 1 wherein the tip electrode and the anode electrode are spaced from one another by a distance in the range of 5 to 17 mm.

6. The LIMD of claim 1 wherein the anode electrode is coated with a low-polarization coating by an amount sufficient to reduce polarization due to pacing pulses to acceptable levels for capture verification.

7. The method of claim 6 wherein the low-polarization coating includes one or more of tin, iridium oxide, and platinum black.

8. The LIMD of claim 1 wherein the anode electrode comprises a cylindrical portion of the case that is substantially electrically un-insulated.

9. The LIMD of claim 8 wherein the anode portion of the case has a length in the range of 7 to 8 mm from a proximal to a distal end.

10. The LIMD of claim 8 wherein at least a portion of the case, excluding the anodal portion, is coated with a material sufficient to render it substantially electrically inert.

11. The LIMD of claim 10 wherein the material coating the portion of the case excluding an uninsulated anodal portion is perylene.

12. The LIMD of claim 1 wherein the LIMD further comprises a single feedthrough connecting the cathode electrode to the pulse generator and to the sensing system.

13. The LIMD of claim 1 configured for implant within the right ventricle of the heart of the patient.

14. The LIMD of claim 1 further comprising a voltage halver equipped to selectively half a voltage of power generated by a power supply of the device prior to generation of a cathodal stimulation pulse.

15. The LIMD of claim 14 wherein the voltage halver is selectively invoked for pulses of 1.25 volts or less.

16. A system for use with a leadless implantable medical device (LIMD) for implant within a patient, the LIMD having a tip electrode and an anode electrode, the system comprising:
    means for generating a cathodal stimulation pulse with anodal recharge for delivery to patient tissues using the tip electrode and the anode electrode, wherein the anode electrode has a surface area of at least 133 mm² to substantially prevent anodal stimulation;
    means for verifying capture of the cathodal stimulation pulse; and means for delivering a cathodal backup stimulation pulse with anodal recharge using the tip electrode and the anode electrode when capture is not verified.

17. A leadless implantable medical device (LIMD) for implant within the heart of a patient, comprising:
   a case, wherein at least a portion of the case being configured as an anode electrode;
   a tip electrode extending from the case;
   a pulse generator coupled to the tip electrode and the anode electrode and equipped to generate a cathodal stimulation pulse for delivery to patient tissues with an anodal recharge;
   a sensing system equipped to sense electrocardiac signals using the tip electrode with reference to the anode electrode; and
   an automatic capture verification system operative to verify capture of the cathodal stimulation pulse based on sensed electrocardiac signals, wherein the automatic capture verification system includes a biquad amplifier coupled to the sensing system with a center frequency and a Q value sufficient to detect a positive derivative within the electrocardiac signals to verify capture.

18. The LIMD of claim 17 wherein the center frequency of the biquad amplifier is about 50 hertz and the Q value of the biquad amplifier is about 1.4.

* * * * *